(12) United States Patent
Koehler et al.

(10) Patent No.: US 10,064,586 B2
(45) Date of Patent: Sep. 4, 2018

(54) PROJECTION DATA ACQUISITION APPARATUS

(71) Applicant: KONINKLIJKE PHILIPS N.V., Eindhoven (NL)

(72) Inventors: Thomas Koehler, Norderstedt (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 333 days.

(21) Appl. No.: 15/104,003

(22) PCT Filed: Dec. 5, 2014

(86) PCT No.: PCT/EP2014/076768
§ 371 (c)(1),
(2) Date: Jun. 13, 2016

(87) PCT Pub. No.: WO2015/091031
PCT Pub. Date: Jun. 25, 2015

(65) Prior Publication Data
US 2016/0287191 A1 Oct. 6, 2016

(30) Foreign Application Priority Data
Dec. 17, 2013 (EP) .................................... 13197755

(51) Int. Cl.
*G01N 23/00* (2006.01)
*A61B 6/03* (2006.01)
(Continued)

(52) U.S. Cl.
CPC .............. *A61B 6/035* (2013.01); *A61B 6/032* (2013.01); *A61B 6/4476* (2013.01);
(Continued)

(58) Field of Classification Search
CPC ........... A61B 6/027; A61B 6/032; A61B 8/15; G06T 11/001; G01T 1/2985
See application file for complete search history.

(56) References Cited

U.S. PATENT DOCUMENTS

| 7,206,441 B2 | 4/2007 | Koehler | |
|---|---|---|---|
| 2003/0179918 A1 | 9/2003 | Kohler | |
| 2008/0056437 A1* | 3/2008 | Pack | ..................... G01T 1/2985 378/10 |

FOREIGN PATENT DOCUMENTS

WO 2010/061332 6/2010

OTHER PUBLICATIONS

Kaestner et al., "Spatiotemporal computed tomography of dynamic processes", Optical Engineering, vol. 50 (12), pp. 123201-1 to 123201-9 (2011).
(Continued)

*Primary Examiner* — Don Wong (57) ABSTRACT

The invention relates to a projection data acquisition apparatus (14) for acquiring projection data for being used for reconstructing a computed tomography image. In acquisition intervals projection data are acquired only at certain acquisition rotational positions of a radiation source (2) relative to an object, wherein an acquisition rotational position of a current acquisition interval divides a largest non-acquisition angular region covering rotational positions, at which projection data have not already been acquired, into two smaller non-acquisition angular regions. Because of this acquisition of the projection data, after each acquisition interval the acquisition rotational positions, at which projection data have been acquired already, are relatively homogeneously distributed. This allows for an improved image quality of a computed tomography image which is reconstructed based on the acquired projection data.

13 Claims, 6 Drawing Sheets

(51) Int. Cl.
   *G01N 23/046*   (2018.01)
   *G06T 11/00*    (2006.01)
   *A61B 6/00*     (2006.01)

(52) U.S. Cl.
   CPC ............ *A61B 6/5205* (2013.01); *A61B 6/541* (2013.01); *G01N 23/046* (2013.01); *G06T 11/003* (2013.01); *A61B 6/503* (2013.01); *A61B 6/5258* (2013.01); *A61B 6/5288* (2013.01)

(56) References Cited

OTHER PUBLICATIONS

Speidel, et al., "ECG-gated HYPR reconstruction for undersampled CT myocardial perfusion imaging", Proceedings of SPIE, vol. 6510, Medical Imaging 2007: Physics of Medical Imaging, San Diego, CA, USA, 651014 (2007).

Isola, et al., "Motion-compensated iterative cone-beam CT image reconstruction with adapted blobs as basis functions", Physics in Medicine and Biology, vol. 53, pp. 6777 to 6797 (2008).

Schomberg, "Time-Resolved Cardiac Cone-Beam CT", Proceedings of the 9th International Meeting on Fully Three-Dimensional Image Reconstruction in Radiology and Nuclear Medicine, pp. 362 to 365 (2007).

Winkelmann, et al., "An Optimal Radial Profile Order Based on the Golden Ratio for Time-Resolved MRI", IEEE Transactions on Medical Imaging, vol. 26, No. 1, Jan. 2007.

Manzke, et al., "Adaptive temporal resolution optimization in helical cardiac cone beam CT reconstruction", 2003 American Association of Physicists in Medicine.

\* cited by examiner

PROJECTION DATA ACQUISITION APPARATUS

CROSS REFERENCE TO RELATED APPLICATIONS

This application is the U.S. National Phase application under 35 U.S.C. § 371 of International Application No. PCT/EP2014/076768, filed Dec. 5, 2014, published as WO 2015/091031 on Jun. 25, 2015, which claims the benefit of European Patent Application Number 13197755.5 filed Dec. 17, 2013. These applications are hereby incorporated by reference herein.

FIELD OF THE INVENTION

The invention relates to a projection data acquisition apparatus, method and computer program for acquiring projection data of an object. The invention relates further to a computed tomography apparatus for generating a computed tomography image of the object, which comprises the projection data acquisition apparatus.

BACKGROUND OF THE INVENTION

The article "Spatiotemporal computed tomography of dynamic processes" by A. Kaestner et al., Optical Engineering, volume 50 (12), pages 123201-1 to 123201-9 (2011) discloses a computed tomography system which uses non-sequential acquisition schemes for acquiring projection data, wherein a computed tomography image is reconstructed based on the acquired projection data. The computed tomography system is particularly adapted to use a binary decomposition acquisition scheme and a golden-ratio decomposition acquisition scheme.

The article "ECG-gated HYPR reconstruction for undersampled CT myocardial perfusion imaging" by M. A. Speidel et al., Proceedings of SPIE, volume 6510, Medical Imaging 2007: Physics of Medical Imaging, San Diego, Calif., USA, 651014 (2007) discloses a projection data acquisition apparatus for acquiring projection data to be used for reconstructing a computed tomography (CT) image. The projection data acquisition apparatus comprises an x-ray source for generating x-rays traversing an object to be imaged, an x-ray detector for detecting the x-rays after having traversed the object and for generating projection data based on the detected x-rays, and a moving unit for moving the x-ray source around the object. The projection data acquisition apparatus is adapted to acquire in each rotation projection data at each n-th acquisition rotational position of the x-ray source only, wherein the acquisition rotational positions, at which the projection data are acquired, are advanced by one rotational position after each rotation. The acquired projection data are used together with an electrocardiography (ECG) signal, which is measured during the acquisition of the projection data, for reconstructing an ECG-gated computed tomography image. Since the projection data acquired during few, especially two, subsequent rotations are very inhomogeneously distributed, the image quality of the reconstructed computed tomography image may be relatively low.

SUMMARY OF THE INVENTION

It is an object of the invention to provide a projection data acquisition apparatus, method and computer program for acquiring projection data of an object, which allow for reconstructing a computed tomography image having an improved image quality. It is a further object of the present invention to provide a computed tomography apparatus for generating a computed tomography image of an object, which comprises the projection data acquisition apparatus.

In a first aspect of the present invention a projection data acquisition apparatus for acquiring projection data of an object is presented, wherein the projection data acquisition apparatus comprises:

- a radiation source for generating radiation for traversing the object,
- a detector for detecting the radiation after having traversed the object and for generating the projection data based on the detected radiation,
- a moving unit for moving the radiation source and the object relative to each other, wherein the movement includes several rotations of the radiation source around the object,
- a control unit for controlling the radiation source and the moving unit such that:
    in acquisition intervals projection data are acquired only at certain acquisition rotational positions of the radiation source relative to the object, wherein an acquisition rotational position of a current acquisition interval divides a largest non-acquisition angular region covering rotational positions, at which projection data have not already been acquired, into two smaller non-acquisition angular regions,
    the angular distances between acquisition rotational positions of an n-th acquisition interval are equal to the angular distances between acquisition rotational positions of an (n−1)-th acquisition interval, wherein the angular distances between acquisition rotational positions of an acquisition interval are equal to a k-th Fibonacci number, wherein the rotational positions of an acquisition interval are consecutively numbered and an angular distance between rotational positions is defined by the difference between the rotational positions in terms of their numbers, and
    the first acquisition rotational position of the n-th acquisition interval is equal to (n times the (k−1)-th Fibonacci number) modulo the k-th Fibonacci number, wherein the rotational positions of an acquisition interval are consecutively numbered starting from zero.

Since an acquisition rotational position of a current acquisition interval divides a largest non-acquisition angular region covering rotational positions, at which projection data have not already been acquired, into two smaller non-acquisition angular regions, after each acquisition interval the acquisition rotational positions, at which projection data have been acquired already, are relatively homogeneously distributed. This allows for an improved image quality of a computed tomography image reconstructed based on the acquired projection data. In particular, since the acquisition rotational positions are relatively homogenously distributed even across different acquisition intervals, it is possible to reconstruct retrospectively computed tomography images based on projection data from any angular range with high image quality.

The radiation source is preferentially an x-ray source, in particular, a grid-switch x-ray tube. Correspondingly, the detector is preferentially adapted to detect x-rays. The radiation source and the detector are preferentially arranged at opposing sides of a gantry surrounding an examination region in which the object is to be located. The gantry is preferentially adapted to be rotated around the examination region, in order to move the radiation source around the object. The moving unit preferentially comprises a motor for rotating the gantry.

The rotational positions are preferentially discrete rotational positions, wherein the control unit is preferentially adapted such that the respective largest non-acquisition angular region is divided into two smaller non-acquisition angular regions, wherein each of the smaller non-acquisition angular regions includes at least one rotational position, at which projection data have not already been acquired, as long as the respective largest non-acquisition angular region covers three or more of the discrete rotational positions, at which projection data have not already been acquired. If regarding the current acquisition interval several largest non-acquisition angular regions covering rotational positions, at which projection data have not already been acquired, are present, only one, several or all of these non-acquisition angular regions may be divided into two smaller non-acquisition angular regions during the current acquisition interval.

In an embodiment the control unit is adapted to control the radiation source and the moving unit such that an acquisition interval corresponds to a rotation of the radiation source around the object. During acquiring the projection data all projection data corresponding to the same acquisition rotational position, but to different rotations, may be regarded as being redundant with respect to an image point as long as the image point is traversed by the radiation. It can therefore be advantageous to avoid the acquisition of projection data which correspond to the same acquisition rotational position, but to different rotations, wherein the distribution of acquisition rotational positions of subsequent rotations should still be relatively homogeneous. This can be achieved, if an acquisition rotational position of a current rotation divides a largest non-acquisition angular region covering rotational positions, at which projection data have not already been acquired, into two smaller non-acquisition angular regions.

In an embodiment the object is a periodically moving object and the projection data acquisition apparatus further comprises a moving period determination unit for determining moving periods of the movement of the object, wherein the control unit is adapted to the control the radiation source and the moving unit such that an acquisition interval corresponds to a moving period of the movement of the object. If, for instance, a gated multi-cycle reconstruction is performed, the image quality may be reduced, if the acquisition rotational positions of subsequent moving periods match. It can therefore be advantageous to avoid such a matching, wherein the distribution of acquisition rotational positions of subsequent moving periods should still be relatively homogeneous. This can be achieved, if an acquisition rotational position of a current moving period divides a largest non-acquisition angular region covering rotational positions, at which projection data have not already been acquired, into two smaller non-acquisition angular regions.

The object is preferentially a part of a human being like a person or an animal, which moves due to cardiac motion and/or due to breathing. This part might be, for instance, a tumor or a part comprising the tumor. The moving period determination unit may be adapted to determine a cardiac moving period describing a moving period caused by cardiac motion and/or a breathing moving period describing a movement caused by respiratory motion. The moving period determination unit may comprise an ECG device or another device for generating a signal being indicative of the cardiac motion. Alternatively or in addition, the moving period determination unit may comprise a respiratory belt or another means for determining a signal being indicative of the respiratory motion.

The control unit is preferentially adapted to control the radiation source and the moving unit such that an acquisition rotational position of a current acquisition interval divides a largest non-acquisition angular region in accordance with the golden ratio. If the respective largest non-acquisition angular region is divided in accordance with the golden ratio, the sampling pattern defined by the acquisition rotational positions of two or more subsequent acquisition intervals can be the same apart from different starting angles. This allows for a very efficient acquisition of the projection data.

It is preferred that the control unit is adapted to control the radiation source and the moving unit such that the angular distances between acquisition rotational positions of a current acquisition interval are equal to the angular distances between acquisition rotational positions of a previous acquisition interval and such that the angular offsets of a first acquisition rotational position of a current acquisition interval relative to a rotational position at the beginning of the current acquisition interval and a first acquisition rotational position of a previous acquisition interval relative to a rotational position at the beginning of the previous acquisition interval are different. The angular distances between acquisition rotational positions of an acquisition interval are equal to a Fibonacci number, wherein the rotational positions of an acquisition interval are discrete and consecutively numbered and an angular distance between rotational positions is defined by the difference between the rotational positions in terms of their numbers.

It is further preferred that the control unit is adapted to control the radiation source and the moving unit such that an angular offset between a) a first acquisition rotational position of a current acquisition interval relative to a rotational position at the beginning of the current acquisition interval and b) a first acquisition rotational position of a previous acquisition interval, particularly of an immediately previous acquisition interval, relative to a rotational position at the beginning of the previous acquisition interval is equal to a Fibonacci number, wherein the rotational positions of an acquisition interval are discrete and consecutively numbered and an angular distance between rotational positions is defined by the difference between the rotational positions in terms of their numbers.

The control unit is adapted to control the radiation source and the moving unit such that a) the angular distances between acquisition rotational positions of an n-th acquisition interval are equal to the angular distances between acquisition rotational positions of an (n−1)-th acquisition interval, wherein the angular distances between acquisition rotational positions of an acquisition interval are equal to a k-th Fibonacci number, wherein the rotational positions of an acquisition interval are discrete and consecutively numbered and an angular distance between rotational positions is defined by the difference between the rotational positions in terms of their numbers, and b) the first acquisition rotational position of the n-th acquisition interval is equal to (n times the (k−1)-th Fibonacci number) modulo the k-th Fibonacci number, wherein the rotational positions of an acquisition interval are discrete and consecutively numbered starting from zero. If the projection data are acquired in this way based on the Fibonacci numbers, an acquisition of the projection data in accordance with the golden ratio is approximated, which leads to a very homogeneous angular distribution of the acquisition rotational positions.

The movement of the radiation source relative to the object can be a circular movement, i.e. the radiation source can be moved along a circular trajectory around the object. However, the movement between the radiation source and the object can also be another movement, which includes a rotation. For instance, the moving unit can be adapted to move the radiation source and the object relative to each other such that the movement also includes a translational movement of the radiation source and the object relative to each other, i.e. the radiation source may be moved relative to the object along a helical trajectory or another trajectory including a rotation and a translation.

In a further aspect of the present invention a computed tomography apparatus for generating a computed tomography image of an object is presented, wherein the computed tomography apparatus comprises:
- a projection data acquisition apparatus for acquiring projection data of the object as defined in claim 1,
- a reconstruction unit for reconstructing the computed tomography image based on the acquired projection data.

Preferentially, the reconstruction unit is adapted to iteratively reconstruct the computed tomography image. The iterative reconstruction algorithm has less stringent angular sampling requirements with respect to sampling density and sampling uniformity, which can therefore lead to computed tomography images having an improved image quality. The object may be a periodically moving object and the projection data acquisition apparatus may further comprise a moving period determination unit for determining moving periods of the movement of the object, wherein the reconstruction unit may be adapted to reconstruct the computed tomography image based on the acquired projection data and the determined moving periods. For instance, the reconstruction unit can be adapted to perform a gated reconstruction algorithm, wherein for reconstructing the image only projection data are used, which correspond to a certain part of the moving period, i.e. to a certain gating window. This can lead to a further improved quality of the reconstructed computed tomography image.

In another aspect of the present invention a projection data acquisition method for acquiring projection data of an object is presented, wherein the projection data acquisition method comprises:
- generating radiation for traversing the object by a radiation source,
- detecting the radiation after having traversed the object and generating the projection data based on the detected radiation by a detector,
- moving the radiation source and the object relative to each other by a moving unit, wherein the movement includes several rotations of the radiation source around the object, and
- controlling the radiation source and the moving unit by a control unit such that:
  in acquisition intervals projection data are acquired only at certain acquisition rotational positions of the radiation source relative to the object, wherein an acquisition rotational position of a current acquisition interval divides a largest non-acquisition angular region covering rotational positions, at which projection data have not already been acquired, into two smaller non-acquisition angular regions,
  the angular distances between acquisition rotational positions of an n-th acquisition interval are equal to the angular distances between acquisition rotational positions of an (n−1)-th acquisition interval, wherein the angular distances between acquisition rotational positions of an acquisition interval are equal to a k-th Fibonacci number, wherein the rotational positions of an acquisition interval are consecutively numbered and an angular distance between rotational positions is defined by the difference between the rotational positions in terms of their numbers, and
  the first acquisition rotational position of the n-th acquisition interval is equal to (n times the (k−1)-th Fibonacci number) modulo the k-th Fibonacci number, wherein the rotational positions of an acquisition interval are consecutively numbered starting from zero.

In a further aspect of the present invention a projection data acquisition computer program for acquiring projection data of an object is presented, wherein the projection data acquisition computer program comprises program code means for causing a projection data acquisition apparatus as defined in claim 1 to carry out the steps of the projection data acquisition method as defined in claim 12, when the projection data acquisition computer program is run on the control unit of the projection data acquisition apparatus.

It shall be understood that the projection data acquisition apparatus of claim 1, the computed tomography apparatus of claim 9, the projection dated acquisition method of claim 12, and the computer program of claim 13 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
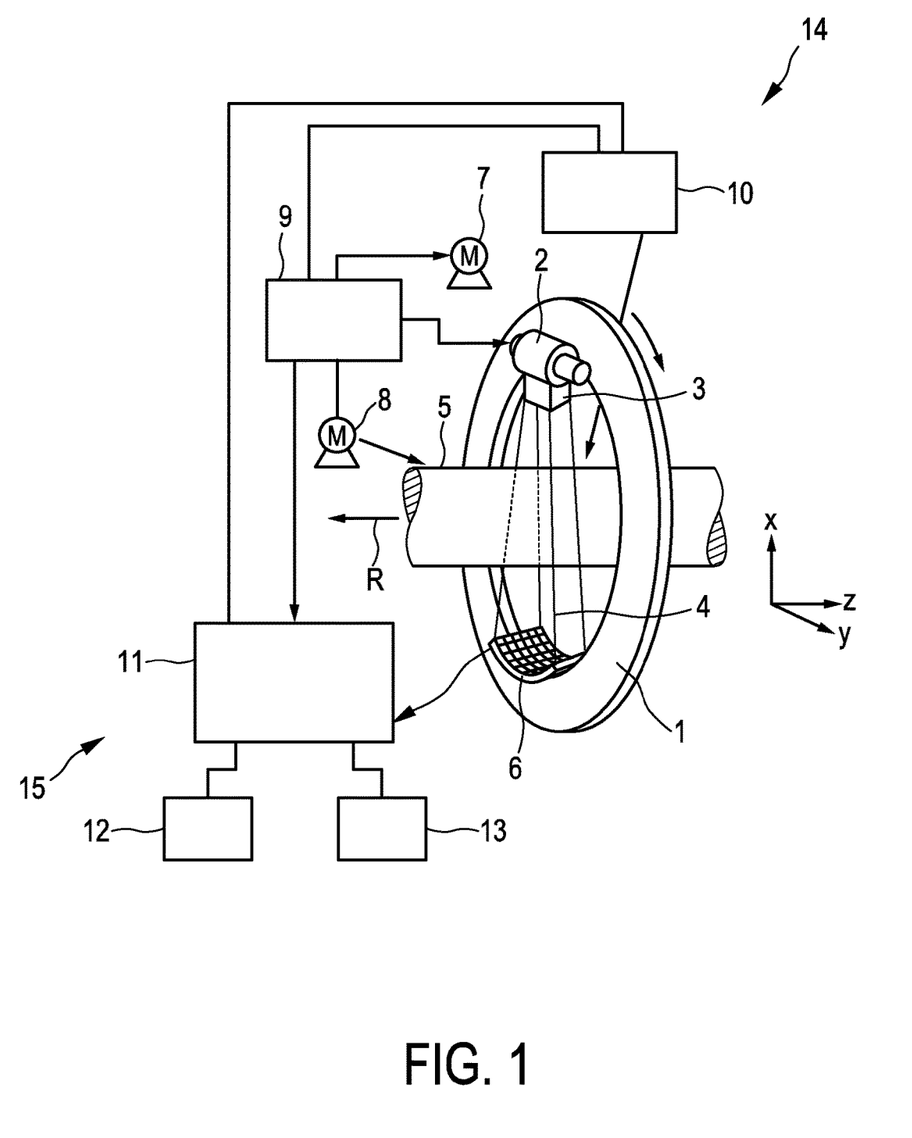
FIG. 1 shows schematically and exemplarily an embodiment of a computed tomography apparatus for generating a computed tomography image of an object, FIGS. 2 to 4 schematically and exemplarily illustrate sampling patterns for acquiring projection data.

FIG. 1 shows schematically and exemplarily a computed tomography apparatus 15 for generating a computed tomography image of an object. The computed tomography apparatus 15 comprises a projection data acquisition apparatus 14 for acquiring projection data of the object and a reconstruction unit 11 for reconstructing the computed tomography image based on the acquired projection data. The reconstructed computed tomography image can then be shown on a display 13. The computed tomography apparatus 15 further comprises an input unit 12 like a keyboard, a computer mouse, a touch pad, et cetera, in order to allow a user to input commands for, for instance, starting an acquisition of projection data, to input parameters like acquisition parameters or reconstruction parameters, et cetera.

The projection data acquisition apparatus 14 includes a gantry 1 which is capable of rotation about a rotational axis R which extends parallel to a z direction. A radiation source 2, which is, in this embodiment, a grid-switch x-ray tube, is mounted on the gantry 1. The radiation source 2 is provided with a collimator 3, which forms, in this embodiment, a conical radiation beam 4 from the radiation generated by the radiation source 2. The radiation traverses the object (not shown), such as a part of a patient comprising a tumor or another region of interest, within an examination zone 5 being, in this embodiment, cylindrical. After having traversed the examination zone 5 the radiation beam 4 is incident on a detector 6, which comprises a two-dimensional detection surface, wherein also the detector 6 is mounted on the gantry 1.

The projection data acquisition apparatus 14 further comprises two motors 7, 8. The gantry is driven at a preferably constant but adjustable angular speed by the motor 7. The motor 8 is provided for displacing the object, which is preferentially arranged on a support means like a patient table, parallel to the direction of the rotational axis R or the z axis. These motors 7, 8 are controlled by a control unit 9 such that the radiation source 2 and the object move relatively to each other along, for instance, a helical trajectory. However, it is also possible that the object is not moved, but that only the radiation source 2 is rotated, i.e. that the radiation source 2 moves along a circular trajectory relative to the object. Furthermore, in another embodiment the collimator 3 can be adapted to form another beam shape, in particular a fan beam, and the detector 6 can comprise a detection surface, which is shaped corresponding to the other beam shape, in particular, to the fan beam.

During the relative movement of the radiation source 2 and the object the detector 6 generates projection data depending on the radiation incident on the detection surface of the detector 6. The acquired projection data are provided to the reconstruction unit 11 for allowing the reconstruction unit 11 to reconstruct the computed tomography image based on the acquired projection data. The control unit 9 may be adapted to also control the reconstruction unit 11. However, also a further control unit can be provided for controlling the reconstruction unit 11 or for controlling other components of the computed tomography apparatus 15.

Since the motors 7, 8 move the radiation source 2 and the object relative to each other, they can be regarded as forming a moving unit for moving the radiation source 2 and the object relative to each other, wherein the movement includes several rotations of the radiation source 2 around the object. The control unit 9 is adapted to control the radiation source 2 and the moving unit, i.e. the motors 7, 8, such that in acquisition intervals projection data are acquired only at certain acquisition rotational positions of the radiation source 2 relative to the object, i.e. at certain rotational positions of the gantry, wherein an acquisition rotational position of a current acquisition interval divides a largest non-acquisition angular region covering rotational positions, at which projection data have not already been acquired, into two smaller non-acquisition angular regions. If several largest non-acquisition angular regions covering rotational positions, at which projection data have not already been acquired, are present, in the current acquisition interval one, several or all of these largest non-acquisition angular regions may be divided into two smaller non-acquisition angular regions. Preferentially, as long as the respective largest non-acquisition angular region covers at least four or at least three rotational positions, at which projection data have not already been acquired, the respective largest non-acquisition angular region is divided into two smaller non-acquisition angular regions. If the respective largest non-acquisition angular region covers only two rotational positions, the respective largest non-acquisition angular region can of course not be divided into two smaller non-acquisition angular regions. In this case in the current acquisition interval at one of the rotational positions of the respective largest non-acquisition angular region projection data are acquired. The same applies to a respective largest non-acquisition angular region covering only a single rotational position, at which projection data have not already been acquired.

In this embodiment the control unit 9 is adapted to control the radiation source 2 and the moving unit 7, 8 such that an acquisition interval corresponds to a rotation of the radiation source 2 around the object. However, especially if the object is a periodically moving object, which is moved due to cardiac motion or respiratory motion, the control unit 9 may be adapted to control the radiation source 2 and the moving unit 7, 8 such that an acquisition interval corresponds to a moving period of the movement of the object, which may be provided by a moving period determination unit 10. In this embodiment the moving period determination unit 10 is adapted to generate an ECG signal and to determine the moving period based on the generated ECG signal. In another embodiment the moving period determination unit 10 can also be adapted to determine, for instance, the respiratory motion by using, for example, a respiratory belt.

The control unit 9 may be adapted to control the radiation source 2 and the moving unit 7, 8 such that the acquisition rotational positions of a current acquisition interval, i.e. the rotational positions of a current acquisition interval at which projection data are acquired, divide the largest non-acquisition angular regions in accordance with the golden ratio, i.e. one of the two smaller non-acquisition angular regions covers about 61.8 percent of the previous largest non-acquisition angular region that has been divided and the other smaller non-acquisition angular region covers about 38.2 percent of the previous largest non-acquisition angular region, wherein it is tried to obtain these proportions as good as possible under consideration of the available discrete rotational positions within the current acquisition interval, at which projection data can be acquired, i.e. under consideration of the discrete rotational sampling positions.

The control unit 9 is preferentially adapted to control the radiation source 2 and the moving unit 7, 8 such that angular distances between acquisition rotational positions of a current acquisition interval are equal to the angular distances between acquisition rotational positions of a previous acquisition interval, especially of the immediately previous acquisition interval, and such that the angular offsets of a first acquisition rotational position of a current acquisition interval relative to a rotational position at the beginning of the current acquisition interval and a first acquisition rotational position of the previous acquisition interval, i.e. of an immediately previous acquisition interval, relative to a rotational position at the beginning of the previous acquisition interval are different. In particular, the angular distances between acquisition rotational positions of an acquisition interval may be equal to a Fibonacci number, wherein the discrete rotational positions of an acquisition interval are consecutively numbered and an angular distance between rotational positions is defined by the difference between the rotational positions in terms of their numbers. Moreover, preferentially the control unit 9 is adapted to control the radiation source 2 and the moving unit 7, 8 such that an angular offset between a) a first acquisition rotational position of a current acquisition interval relative to a rotational position at the beginning of the current acquisition interval and b) a first acquisition rotational position of a previous acquisition interval, i.e. of the immediately previous acquisition interval, relative to a rotational position at the beginning of the previous acquisition interval is equal to a Fibonacci number, wherein the discrete rotational positions of an acquisition interval are consecutively numbered and an angular distance between rotational positions is defined by the difference between the rotational positions in terms of their numbers.

Figure 2:
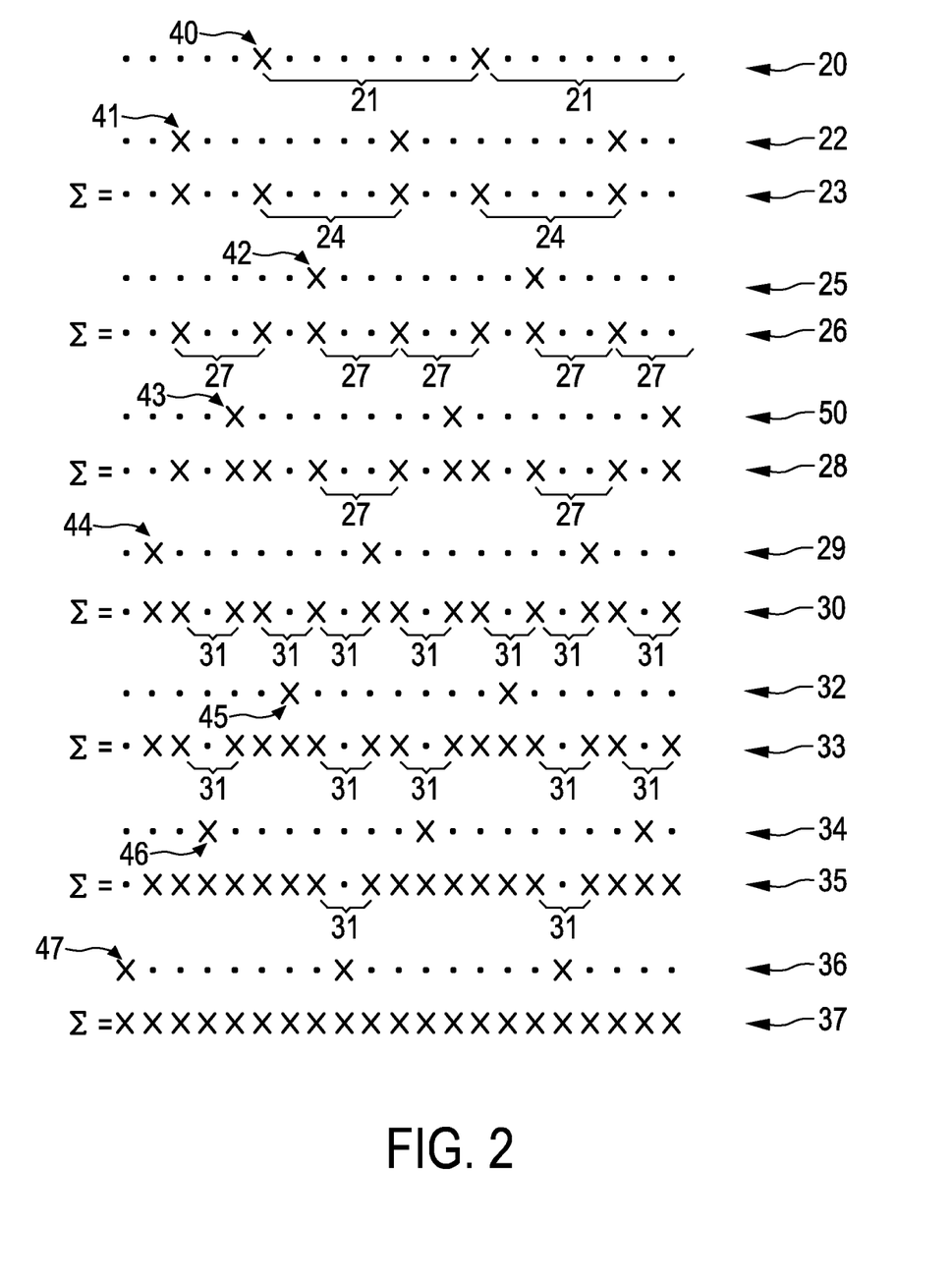

In an embodiment the control unit 9 is adapted to control the radiation source 2 and the moving unit 7, 8 such that the angular distances between acquisition rotational positions of an n-th acquisition interval are equal to the angular distances between acquisition rotational positions of an (n−1)-th acquisition interval, wherein the angular distances between acquisition rotational positions of an acquisition interval are equal to a k-th Fibonacci number $F(k)$, and such that a first acquisition rotational position $I_n$ of the n-th acquisition interval is defined by following equation:

$$I_n=[nF(k-1)] \bmod F(k),$$

wherein $F(k-1)$ defines the $(k-1)$-th Fibonacci number with $F(1)=0$, $F(2)=1$, $F(3)=1$, $F(4)=2$, $F(5)=3$, $F(6)=5$, $F(7)=8$ et cetera, mod is the modulo operator and the rotational positions within the respective n-th acquisition interval are discrete and consecutively numbered starting from zero. In the following this Fibonacci number based sampling during the acquisition of the projection data will exemplarily be described with reference to FIG. 2.

In the example illustrated in FIG. 2 an acquisition interval includes 21 discrete rotational positions, wherein in FIG. 2 the dots indicate rotational positions, at which projection data are not acquired or have not been acquired, and the crosses indicate rotational positions, at which the projection data are acquired in the current acquisition interval or have already been acquired. The acquisition intervals comprise 21 rotational positions for illustrative purposes only. In real an acquisition interval may comprise more than 21 rotational positions. For instance, if the acquisition interval is defined by a complete rotation of the radiation source 2 around the object, the number of discrete rotational positions of an acquisition interval may be in the range of one thousand or several thousands. Moreover, in an embodiment the numbers of rotational positions of different acquisition intervals may be different, especially if the acquisition intervals are defined by moving periods, which might be slightly different.

In the example illustrated in FIG. 2 k is 7 such that the angular distance between acquisition rotational positions of an n-th acquisition interval is equal to 8 ($F(7)=8$). These angular distances 21 are shown, for instance, in line 20 of FIG. 2. The line 20 indicates the first acquisition interval such that the first acquisition rotational position 40 is 1·$F(6)$ mod $F(7)=5$, wherein the rotational positions are consecutively numbered starting with zero. In the next acquisition interval shown in line 22, the angular distance between acquisition rotational positions is still $F(7)$, but the first acquisition rotational position 41 of the second acquisition interval is equal to 2 (2·$F(6)$ mod $F(7)=2$). Line 23 indicates the acquisition rotational positions after two acquisition intervals, wherein the largest non-acquisition angular regions are indicated by the reference number 24. In the third acquisition interval shown in line 25 the first acquisition rotational position 42 is 7 (3·$F(6)$ mod $F(7)=7$), which results in the acquisition rotational positions shown in line 26, which are present after three acquisition intervals. In this line 26 the largest non-acquisition angular regions are indicated by reference number 27. In the fourth acquisition interval the first acquisition rotational position 43 is 4 (4·$F(6)$ mod $F(7)=4$) as shown in line 50, which results, after the fourth acquisition interval has been completed, in the acquisition rotational positions shown in line 28, showing the remaining largest non-acquisition angular regions 27. In the fifth acquisition interval the first acquisition rotational position 44 is 1 (5·$F(6)$ mod $F(7)=1$) as shown in line 29, which results, after the fifth acquisition interval has been completed, in the acquisition rotational positions shown in line 30 with the largest non-acquisition angular regions 31. In the sixth acquisition interval shown in line 32 the first acquisition rotational position 45 is 6 (6·$F(6)$ mod $F(7)=6$), which results, after the sixth acquisition interval has been completed, in the acquisition rotational positions shown in line 33 including the remaining largest non-acquisition angular regions 31. In the seventh acquisition interval the first acquisition rotational position 46 is 3 (7·$F(6)$ mod $F(7)=3$) as shown in line 34, which results in the acquisition rotational positions shown in line 35 with the remaining largest non-acquisition angular regions 31. Finally, in the eighth acquisition interval indicated in line 36 the first acquisition rotational position 47 is 0 (8·$F(6)$ mod $F(7)=0$) such that the acquisition rotational positions are at the positions 0, 8 and 16 in line 36. After the eighth acquisition interval has been completed, at all rotational positions projection data have been acquired as shown in line 37.

Figure 3:
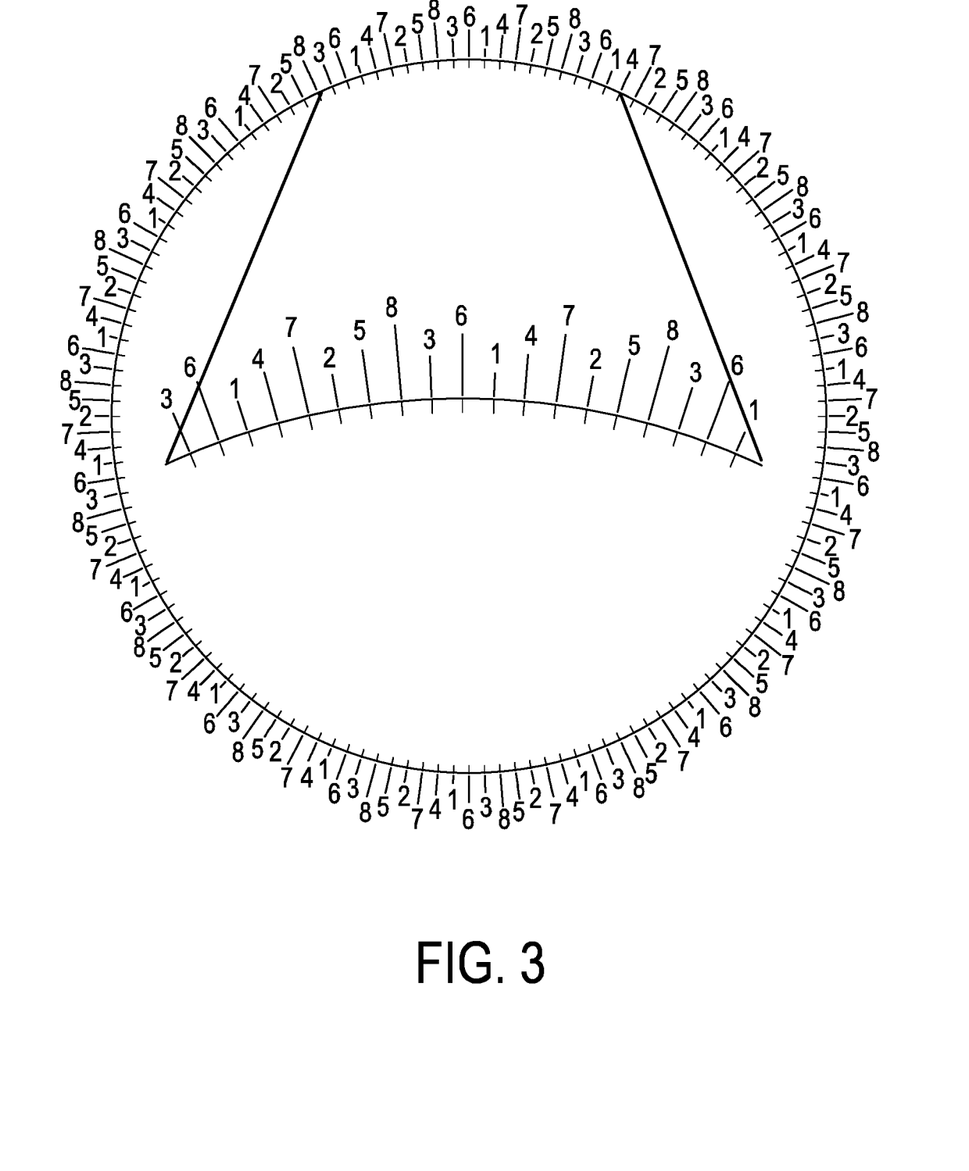
Figure 4:
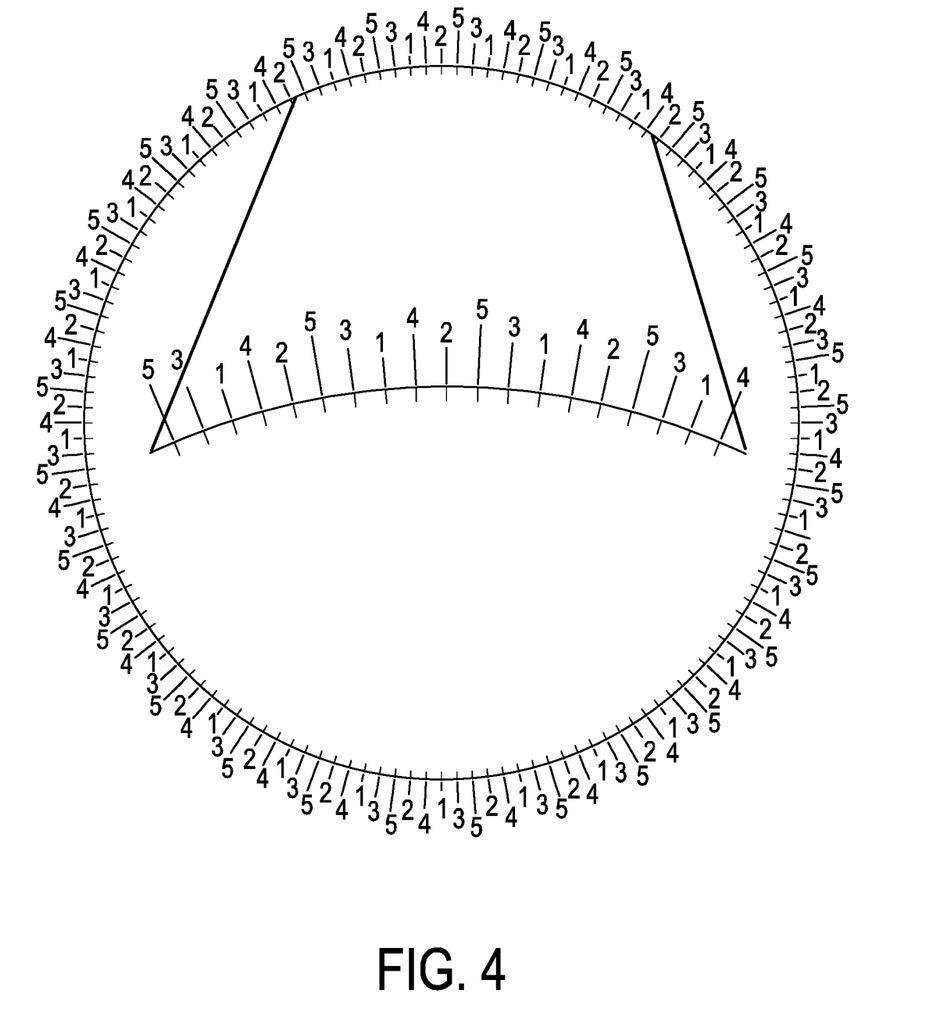

FIG. 3 shows schematically and exemplarily a further illustration of a sampling of the rotational positions, wherein in this example an acquisition interval is defined by a full rotation of the radiation source 2 around the object, a full rotation corresponds to 144 discrete rotational positions and k is 7. The numbers in FIG. 3 relate to the acquisition intervals, i.e. to the rotations in this embodiment. Thus, during the first rotation projection data are acquired at the rotational positions indicated by the number 1, during the second rotation projection data are acquired at rotational positions indicated by the numbers 2, et cetera. In FIG. 3 inside the circle a part of the circle is shown in a magnified view. FIG. 4 schematically and exemplarily shows a further example, wherein also in this example an acquisition interval corresponds to a complete rotation of a radiation source around the object and covers 144 rotational positions. However, in the example shown in FIG. 4 k is 6.

The reconstruction unit 10 is preferentially adapted to iteratively reconstruct the computed tomography image based on the acquired projection data and the determined moving periods. In particular, the reconstruction unit 11 can be adapted to use for the reconstruction only projection data, which correspond to a certain part of the moving period, i.e. the reconstruction unit can be adapted to perform a gated reconstruction. Known iterative gated reconstruction algorithms can be used for this reconstruction of the computed tomography image like the reconstruction algorithm disclosed in U.S. Pat. No. 7,596,204 B2, which is herewith incorporated by reference.

Figure 5:
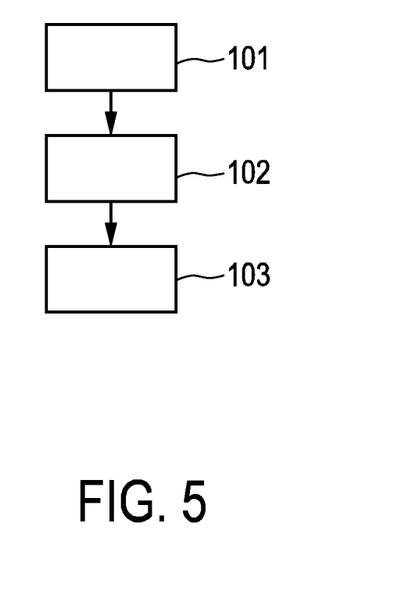
FIG. 5 shows a flowchart exemplarily illustrating an embodiment of a computed tomography method for generating a computed tomography image of an object, and FIG. 6 schematically and exemplarily illustrates temporal resolutions depending on a number of breathing cycles per minute.

In the following an embodiment of a computed tomography method will exemplarily be described with reference to a flowchart shown in FIG. 5.

In step 101 the projection data are acquired. Thus, the radiation source 2 generates radiation for traversing the object, the moving unit 7, 8 moves the radiation source 2 and the object relative to each other, wherein the movement includes several rotations of the radiation source 2 around the object, and during the rotation the radiation is detected after having traversed the object and the projection data are generated based on the detected radiation by the detector 6. Moreover, in step 101 the acquisition of the projection data is controlled by the control unit 9 such that in acquisition intervals projection data are acquired only at certain acquisition rotational positions of the radiation source 2 relative to the object, wherein the acquisition rotational positions of a current acquisition interval divide largest non-acquisition angular regions covering rotational positions, at which projection data have not already been acquired, into two smaller non-acquisition angular regions. In particular, in step 101 the projection data can be acquired in accordance with the Fibonacci numbers as described above. This kind of acquiring the projection data performed in step 101 can be regarded as defining a projection data acquisition method for acquiring projection data.

In step 102 the reconstruction unit 11 reconstructs a computed tomography image of the object based on the projection data acquired in step 101 and in step 103 the reconstructed computed tomography image is shown on the display 13.

The reconstruction unit can be adapted to reconstruct for different phases within the moving period different computed tomography images based on the projection data and the determined moving periods, wherein these computed tomography images reconstructed for different moving phases can be regarded as forming a four-dimensional computed tomography image, which may be used for Radiation Therapy Planning (RTP), especially if a tumor to be treated is located in the thorax or abdomen and moves due to breathing. Thus, in an embodiment the object, of which a four-dimensional computed tomography image is reconstructed, can be a tumor or a thorax or abdomen comprising the tumor, wherein the moving period determination unit can be adapted to determine the breathing movement period by using, for instance, a respiratory belt or another means for detecting the breathing period.

If the computed tomography apparatus is adapted to generate a four-dimensional computed tomography image, which should be used for RTP, the computed tomography apparatus is preferentially adapted to provide the four-dimensional computed tomography image with a temporal resolution of about 5 percent to 10 percent of the breathing period, i.e. the temporal resolution is preferentially around 300 to 600 ms for a typical breathing period of 6 s. Although it could be believed that this temporal resolution could be easily achievable, because it seems to be less challenging than, for instance, the requirements for gated cardiac computed tomography imaging, where much higher temporal resolution is required, which might be less than 100 ms, it is actually not, as will in the following be explained with reference to FIG. 6.

Figure 6:
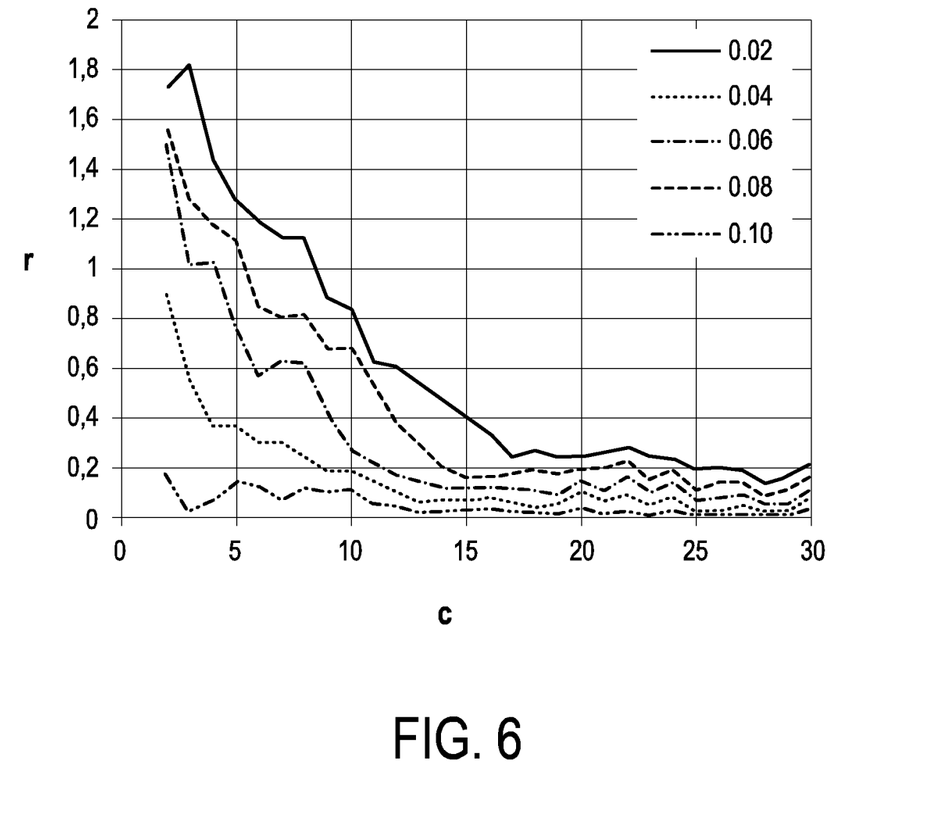

FIG. 6 schematically and exemplarily shows the temporal resolution r as a function of the number c of breathing cycles per minute in seconds for different pitches. In this example the rotation time is fixed to 0.5 s, the reconstruction field of view is set to 500 mm, sparse sampling is not applied and a reconstruction algorithm is used requiring at least 180 degrees of illumination for each image point to be reconstructed. The temporal resolution is defined as the time range of the breathing cycle that is required to reconstruct a computed tomography image at a certain phase point. As can be seen in FIG. 6, if the sparse sampling is not used, at low breathing rates the temporal resolution is not very good. The reason for the strong worsening at low breathing rates is the fact that the gating window for each phase point needs to cover even more than a short scan interval, in order to maintain the sufficiency condition for all voxels in the field of view. This problem may be mitigated by lowering the helical pitch. However, lowering the helical pitch implies that the total dose is distributed over more projection data, which can lead to more pronounced electronic noise in the projection data. This can be avoided by using the sparse sampling scheme, wherein an acquisition rotational position of a current acquisition interval divides a largest non-acquisition angular region covering rotational positions, at which projection data have not already been acquired, into two smaller non-acquisition angular regions.

The radiation source is preferentially a grid-switch x-ray tube. For instance, it might be a grid-switch x-ray tube as disclosed in WO 2010/061332 A1, which is herewith incorporated by reference. However, the radiation source can also be another x-ray tube, in particular, another grid-switch tube, which allows turning on and off the x-ray beam at the different rotational positions. Preferentially, the radiation source is adapted to allow turning on and off the x-ray beam within some microseconds. The switching capability of the radiation source offers the freedom to sample projection data at any desired angular position of the gantry, i.e. at any desired rotational position.

If the x-ray beam were continuously switched on and if the radiation source were moved relative to the object along a helical trajectory, object points would stay within the cone for several rotations, especially in the order of 1/pitch factor, which would lead to a lot of redundancy. Of course, also if the radiation source is moved along a circular trajectory relative to the object, a lot of redundancy would be present. Therefore, it is beneficial to try to place the angular samples such that the samples, i.e. the projection data, from different rotations interleave. Interleaving can provide a much better angular sampling, if the gating window, which may be used by the reconstruction unit for reconstructing the computed tomography image, is widened for reconstruction. A relatively wide reconstruction window may be used in case of generating a motion-averaged computed tomography image, which may be reconstructed for providing an attenuation correction for Positron Emission Tomography (PET) or Single Photon Emission Computed Tomography (SPECT) imaging. A relatively wide gating window may also be used, if a motion compensated reconstruction is performed. In particular, a motion compensated reconstruction algorithm may be used, which estimates the motion within a moving period, which may be defined by a cardiac cycle or a respiratory cycle, by using several gated reconstructed computed tomography images and which feeds this motion information into an iterative reconstruction that incorporates the externally provided motion information. For instance, the motion compensated reconstruction algorithm disclosed in the article "Motion-compensated iterative cone-beam CT image reconstruction with adapted blobs as basis functions" by A. Isola et al., Physics in Medicine and Biology, volume 53, pages 6777 to 6797 (2008) may be used for reconstructing a computed tomography image based on the sparsely sampled projection data. Also other motion compensated reconstruction algorithms may be used like the algorithm disclosed in the article "Time-Resolved Cardiac Cone-Beam CT" by H. Schomberg, Proceedings of the 9th International Meeting on Fully Three-Dimensional Image Reconstruction in Radiology and Nuclear Medicine, pages 362 to 365 (2007), where the motion vector field is jointly estimated with the image at a reference phase.

The computed tomography apparatus is preferentially adapted to use an interleaving scheme derived from Fibonacci numbers, particularly as described above with reference to FIGS. 2 to 4. The interleaving scheme derived from Fibonacci numbers can have the advantage that the sampling pattern is cyclic, which can lead to an overall sampling pattern where any two or more subsequent acquisition intervals have the same sampling pattern. In an embodiment a full angular sampling has N angular samples, i.e. a full acquisition interval comprises N discrete rotational positions. Moreover, in this example the sparsity factor may be l, i.e. only at every l-th rotational position of the N total rotational positions of an acquisition interval projection data are acquired, and on every l-th rotation the sampling pattern repeats itself.

The acquisition intervals can be defined by the rotations of the radiation source around the object, or the acquisition intervals can be defined in another way. In particular, as already mentioned above, an acquisition interval can correspond to a motion period like a cardiac motion period or a breathing motion period. For instance, the sparse sampling can be used for a pulmonary gated reconstruction involving a breathing cycle imposed selection of angular samples. If in an example the rotation time is 0.5 s, the pitch is 0.1 and the breathing period is 2.5 s, an object point will generally stay for 5 s within the radiation cone, covering two breathing cycles. In this scenario the sparse sampling is preferentially provided such that the samples of the two breathing cycles interleave so that the multi-cycle reconstruction benefits from the improved angular sampling. For instance, the same schemes as illustrated in FIGS. 2 to 4 may be used, wherein the sampling offset can be changed at every start of the breathing cycle and not at the starts of new rotations. In order to perform this kind of sampling, a breathing signal provided by the motion period determining unit needs to be fed back to the control unit controlling the radiation source. The sampling pattern can be continuously updated according to the actual breathing cycle length and position.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the reconstruction of the computed tomography image performed by one or several units or devices can be performed by any other number of units or devices. These procedures and/or the control of the computed tomography apparatus in accordance with the computed tomography method and/or the control of the projection data acquisition apparatus in accordance with the projection data acquisition method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a projection data acquisition apparatus for acquiring projection data for being used for reconstructing a computed tomography image. In acquisition intervals projection data are acquired only at certain acquisition rotational positions of a radiation source relative to an object, wherein an acquisition rotational position of a current acquisition interval divides a largest non-acquisition angular region covering rotational positions, at which projection data have not already been acquired, into two smaller non-acquisition angular regions. Because of this acquisition of the projection data, after each acquisition interval the acquisition rotational positions, at which projection data have been acquired already, are relatively homogeneously distributed. This allows for an improved image quality of a computed tomography image which is reconstructed based on the acquired projection data.

The invention claimed is:

1. A projection data acquisition apparatus for acquiring projection data of an object, wherein the projection data acquisition apparatus comprises:
   a radiation source for generating radiation for traversing the object,
   a detector for detecting the radiation after having traversed the object and for generating the projection data based on the detected radiation,
   a moving unit for moving the radiation source and the object relative to each other, wherein the movement includes several rotations of the radiation source around the object,
   a control unit for controlling the radiation source and the moving unit such that:
   in acquisition intervals projection data are acquired only at certain acquisition rotational positions of the radiation source relative to the object, wherein an acquisition rotational position of a current acquisition interval divides a largest non-acquisition angular region covering rotational positions, at which projection data have not already been acquired, into two smaller non-acquisition angular regions,
   the angular distances between acquisition rotational positions of an n-th acquisition interval are equal to the angular distances between acquisition rotational positions of an (n−1)-th acquisition interval, wherein the angular distances between acquisition rotational positions of an acquisition interval are equal to a k-th Fibonacci number, wherein the rotational positions of an acquisition interval are consecutively numbered and an angular distance between rotational positions is defined by the difference between the rotational positions in terms of their numbers, and
   the first acquisition rotational position of the n-th acquisition interval is equal to (n times the (k−1)-th Fibonacci number) modulo the k-th Fibonacci number, wherein the rotational positions of an acquisition interval are consecutively numbered starting from zero.

2. The projection data acquisition apparatus as defined in claim 1, wherein the control unit is adapted to control the radiation source and the moving unit such that an acquisition interval corresponds to a rotation of the radiation source around the object.

3. The projection data acquisition apparatus as defined in claim 1, wherein the object is a periodically moving object and the projection data acquisition apparatus further comprises a moving period determination unit for determining moving periods of the movement of the object, wherein the control unit is adapted to the control the radiation source and the moving unit such that an acquisition interval corresponds to a moving period of the movement of the object.

4. The projection data acquisition apparatus as defined in claim 1, wherein the control unit is adapted to control the radiation source and the moving unit such that an acquisition rotational position of a current acquisition interval divides a largest non-acquisition angular region in accordance with the golden ratio.

5. The projection data acquisition apparatus as defined in claim 1, wherein the control unit is adapted to control the radiation source and the moving unit such that the angular distances between acquisition rotational positions of a current acquisition interval are equal to the angular distances between acquisition rotational positions of a previous acquisition interval and such that the angular offsets of a first acquisition rotational position of a current acquisition interval relative to a rotational position at the beginning of the current acquisition interval and a first acquisition rotational position of a previous acquisition interval relative to a rotational position at the beginning of the previous acquisition interval are different.

6. The projection data acquisition apparatus as defined in claim 1, wherein the control unit is adapted to control the radiation source and the moving unit such that an angular offset between a) a first acquisition rotational position of a current acquisition interval relative to a rotational position at the beginning of the current acquisition interval and b) a first acquisition rotational position of a previous acquisition interval relative to a rotational position at the beginning of the previous acquisition interval is equal to a Fibonacci number, wherein the rotational positions of an acquisition interval are consecutively numbered and an angular distance between rotational positions is defined by the difference between the rotational positions in terms of their numbers.

7. The projection data acquisition apparatus as defined in claim 1, wherein the radiation source is a grid-switch x-ray tube.

8. The projection data acquisition apparatus as defined in claim 1, wherein the moving unit is adapted to move the radiation source and the object relative to each other such that the movement also includes a translational movement of the radiation source and the object relative to each other.

9. A computed tomography apparatus for generating a computed tomography image of an object, the computed tomography apparatus comprising:
    a projection data acquisition apparatus for acquiring projection data of the object as defined in claim 1,
    a reconstruction unit for reconstructing the computed tomography image based on the acquired projection data.

10. The computed tomography apparatus defined in claim 9, wherein the reconstruction unit is adapted to iteratively reconstruct the computed tomography image.

11. The computed tomography apparatus as defined in claim 10, wherein the object is a periodically moving object and the projection data acquisition apparatus further comprises a moving period determination unit for determining moving periods of the movement of the object, wherein the reconstruction unit is adapted to reconstruct the computed tomography image based on the acquired projection data and the determined moving periods.

12. A projection data acquisition method for acquiring projection data of an object, wherein the projection data acquisition method comprises:
    generating radiation for traversing the object by a radiation source,
    detecting the radiation after having traversed the object and generating the projection data based on the detected radiation by a detector,
    moving the radiation source and the object relative to each other by a moving unit, wherein the movement includes several rotations of the radiation source around the object, and
    controlling the radiation source and the moving unit by a control unit such that:
    in acquisition intervals projection data are acquired only at certain acquisition rotational positions of the radiation source relative to the object, wherein an acquisition rotational position of a current acquisition interval divides a largest non-acquisition angular region covering rotational positions, at which projection data have not already been acquired, into two smaller non-acquisition angular regions,
    the angular distances between acquisition rotational positions of an n-th acquisition interval are equal to the angular distances between acquisition rotational positions of an (n−1)-th acquisition interval, wherein the angular distances between acquisition rotational positions of an acquisition interval are equal to a k-th Fibonacci number, wherein the rotational positions of an acquisition interval are consecutively numbered and an angular distance between rotational positions is defined by the difference between the rotational positions in terms of their numbers, and
    the first acquisition rotational position of the n-th acquisition interval is equal to (n times the (k−1)-th Fibonacci number) modulo the k-th Fibonacci number, wherein the rotational positions of an acquisition interval are consecutively numbered starting from zero.

13. A projection data acquisition computer program for acquiring projection data of an object, the projection data acquisition computer program comprising program code means for causing a projection data acquisition apparatus to carry out the steps of the projection data acquisition method as defined in claim 12, when the projection data acquisition computer program is run on the control unit of the projection data acquisition apparatus.

* * * * *